United States Patent [19]

Bagwell

[11] Patent Number: 5,086,653
[45] Date of Patent: Feb. 11, 1992

[54] CAN END TESTING

[75] Inventor: Alan C. Bagwell, Chesterfield, Va.

[73] Assignee: Reynolds Metals Company, Richmond, Va.

[21] Appl. No.: 673,715

[22] Filed: Mar. 22, 1991

[51] Int. Cl.⁵ .............................................. G01N 3/08
[52] U.S. Cl. .................................................... 73/835
[58] Field of Search ............... 73/835, 826; 209/588, 209/936; 414/788.7

[56] References Cited

U.S. PATENT DOCUMENTS

| | | | |
|---|---|---|---|
| 3,633,742 | 1/1972 | Melton | 209/80 |
| 3,700,118 | 10/1972 | Snethen | 214/1 R |
| 3,991,882 | 11/1976 | Fahnestock et al. | 209/73 |
| 4,606,230 | 8/1986 | Scott et al. | 73/826 X |
| 4,637,260 | 1/1987 | Gilliam et al. | 73/826 |
| 4,850,230 | 7/1989 | Eldridge | 73/835 |
| 4,852,745 | 8/1989 | Lemaire et al. | 209/588 |
| 4,938,070 | 7/1990 | Pessina et al. | 73/835 |

Primary Examiner—Jerry W. Myracle
Attorney, Agent, or Firm—Alan T. McDonald

[57] ABSTRACT

There is disclosed apparatus for measuring forces applied to a pull tab during the formation of an opening in a can end having an upper and lower surface with the pull tab hingedly secured to the upper surface and a source line in the can end defining an opening. A sample set of such can ends is batched loaded, by different plant technicians monitoring different can end forming machines, into a feed chute of the testing apparatus. The individual sample sets are separated from each other with special coded can ends. As each can end is fed into the testing apparatus, it is interrogated by a sensing arrangement which determines the presence of a physical characteristic unique to the coded can end signifying the completion of testing of a particular sample set. In this manner, the host computer precisely correlates the test data of each individual can end with relevant production data.

17 Claims, 4 Drawing Sheets

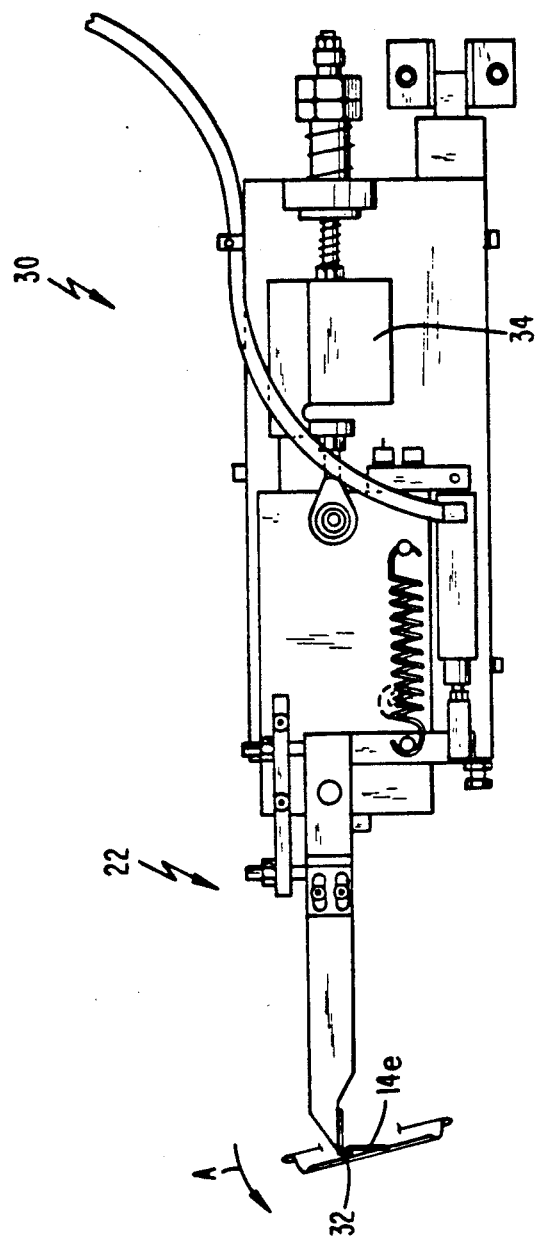
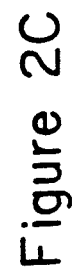
Figure 2A
Figure 2C
Figure 2B

CAN END TESTING

TECHNICAL FIELD

The present invention relates to the manufacture of metal can ends and, more particularly to a coding arrangement for positively correlating quality control test results of one or more sample ends, being tested in a testing machine, with a production run of a particular can end forming machine.

BACKGROUND ART

Non-detachable, easy open metallic can ends are routinely employed in the packaging of beer and soft drinks in metal cans. A representative can end forming machine is disclosed, for example, in U.S. Pat. application Ser. No. 07/104,745, filed Oct. 5, 1987, entitled "Method And Apparatus For Forming Can Ends", assigned to the assignee of the present invention. In such apparatus, ends are blanked from sheet material and formed in a die set. Pull tabs of the type disclosed in U.S. Pat. No. 3,967,752 issued July 6, 1976 assigned to Reynolds Metals Company, are then formed in the can end. The pull tabs may be of the stay-on tab style, as aforementioned, or may be the throw-away tab style, or the complete panel removal style and other styles. In all instances, there should be some resistance to moving the pull tab to form the opening in the container lid but not so much resistance that the opening is too hard to form, or cannot be formed, or too little resistance that the container lid will prematurely open. To ensure customer satisfaction in the forming of openings of container lids, it is practice to test samples of these container lids to ensure that the can end manufacturing apparatus for making the container lids is functioning properly. One such testing apparatus with which the present invention may be employed is disclosed in U.S. Pat. No. 4,850,230, issued July 25, 1989 to Adolph Coors Company, Golden, Colorado, and entitled "Pull Tab Force Measuring Apparatus."

The foregoing can end tester is traditionally used in a can end manufacturing plant wherein numerous can end forming machines are in continuous operation under the supervision, during any particular shift, of different quality control plant technicians or operators who monitor their particular forming machines. One of the responsibilities of these operators is to periodically remove a sample set of can ends from every package or "sleeve" of approximately 480 ends being manufactured. Alternatively, the samples could come from the production line prior to packaging (i.e., real time testing). This sample set is brought by the operator or technician and inserted into the system infeed hopper of the can end tester. The operator/technician will then provide the following information to the can end tester via keyboard input: the operator's clock number (i.e., identifier); the machine number from where the samples were taken; the type of inspection (e.g., opening or tab strength); and the current shift. When the operator/technician is finished, he or she will then return to their normal duties while automated testing occurs.

Since numerous technicians (responsible for different can end forming machines) will be delivering sample ends to the can end tester as part of their normal duties, a backlog is frequently created and it is customary for the technician to place his stack or set of sample ends in the feeder magazine on top of the stack of ends that were already logged in by a different technician. In the prior art, the technician would physically place the ends in the hopper. As each end was fed into the bail assembly during the test cycle, it would be sprayed with a serial number with an ink jet printer. However, there was no means available to the operator to identify a sequential printed number prior to the test nor was there a means to separate the sample sets in the computer generated data. Therefore, the technician could not leave the testing machine unless he somehow marked the leading or trailing can ends in the set and later retrieved these ends in the passed and failed ends bins. Such an end count method of coordinating data to samples was time consuming and subject to data confusion.

SUMMARY OF THE INVENTION

It is accordingly one object of the present invention to enable a host computer of a can end tester to precisely correlate a failed end, from a sample set of ends being tested, with a particular can end forming machine which manufactured that failed end.

Another object of the invention is to enable simultaneous, automated use of the can end tester by a number of different operators or plant technicians having monitoring and/or supervisory responsibility for different can end forming machines at the plant, by allowing a large backlog of samples to be logged into the tester without relying upon the accurate inputting of the actual sample size by the operator.

Still another object is to provide a coding means which informs the computer of the end of a sample set independent of the actual end count.

This invention is used in conjunction with a can end testing apparatus performing a predetermined test on a can end manufactured in a can end forming machine to determine whether the can end satisfies a particular production parameter. The apparatus generally comprises a feed chute into which a set of sample can ends to be tested is inserted as stack. A part feeder removes a next in-line can end to be tested from the stack for delivery to a holder which locates the end in a predetermined location while the test is being performed by a testing arrangement. A storage medium stores data representative of the results of the test. A host computer is capable of retrieving the data from the storage medium and also coordinates the data with production data indicative of at least the machine manufacturing the tested end. After testing, the end is discharged from the testing apparatus. In accordance with the present invention, there is provided a sensing arrangement, located downstream from the feed chute, for sensing the presence of a physical characteristic of a material object positioned in the stack which physical characteristic, when sensed, signifies the completion of testing of a particular sample set. A signal outputted by the sensor arrangement signals the host computer of test completion of the sample set to ensure precise correlation of the test data with the production data.

In the preferred embodiment of the invention, the material object is a coded can end having a preformed hole. The sensing arrangement includes a photoelectric sensor and means for emitting a beam of light onto each can end, including the coded can end, as the ends are sequentially fed from the feed chute. The light beam shines through the hole and reflected by a mirror to impinge on the sensor when the coded end is present.

The sensor then outputs a signal which is processed by the host computer.

The coded can end may also be colored to enable visual identification of different sample sets. Alternatively, the coded can end may be detected utilizing air pressure jet means directed towards the hole. The coded can ends may be bar coded (in lieu of a preformed hole) or metal detection methods may be utilized to determine whether the coded can end having the preformed hole is present within the holding means.

In the preferred embodiment, the can end testing apparatus measures the force applied to a pull tab to form an opening in a container lid. The apparatus comprises a feed chute for holding a supply of container lids, each of which has an upper surface, a lower surface, and a peripheral rim portion and a pull tab on the upper surface which pull tab is adapted to be grasped so as to apply a force thereto to form an opening in the container lid. A holding means holds one of the container lids while testing operations are performed thereon. The holding means has at least one opening so that a substantial portion of the upper surface and all of the pull tab are exposed. A feed means separates one of the container lids from the supply thereof and feeds the one container lid to the holding means. Stop means is provided to position the one container lid and the holding means so that the substantial portion of the upper surface and the pull tab are exposed through the at least one opening. The can end to be tested slides down a ramp from the feed chute to a bail assembly of the holding means where a photoelectric sensor determines that an end is present and another photoelectric sensor sends a beam of light onto the end. If the special coded can end is present, the light shines through the hole (signifying the special coded end) and is reflected back to the sensor. This is the indication that the end of a sample set has occurred and the next end will be a new sample set.

The hole may be approximately 1.25 inches in diameter.

A method of identifying whether the termination of testing a sample set of can ends, manufactured by a particular can end forming machine, has occurred within a can end testing apparatus, is also disclosed. The method comprises the steps of having a plant technician or operator insert the sample set of ends into a system infeed hopper of the can end testing apparatus and then inserting a special coded can end on top of the sample set. The plant technician inputs, via a keyboard, production data (to be correlated with test data) indicative of at least one of the plant technician's identity, the particular machine forming the can end, and the production shift. The testing apparatus then sequentially feeds the end within the set into a predetermined location to perform a predetermined test on the can end. The apparatus also determines completion of testing of the sample set by sensing the feeding of the special coded can end into the testing apparatus.

In accordance with the method of the invention, batches of sets, separated by coded can ends, are inserted into the infeed hopper by different plant technicians monitoring different can end forming machines. The batch testing of the can end sets may therefore be automated since the host computer regulating the testing process reliably coordinates the test data with the production data.

Other automated test machines can also use the special coded end for detecting different sample batches. For example, buckle testing machines for testing the ends for resistance to failure by simulating the internal pressure of the can may utilize the present invention. Machines for testing the can ends for product side coating integrity and machines for testing the ends for their ability to retain the tear strip and tab on the can while it is being opened by the customer may also utilize the principles of the present invention. Likewise, machines which measure quality assurance features to maintain production standards may also utilize the invention.

As mentioned briefly above, special coded can ends for differentiating between sample batches may be detected by sensing other physical characteristics. Metal detection and air pressure resistance of the can ends, sensing the color of a coded can end or a bar code thereon are but representative equivalents of the present invention. The special coded can ends may also be detected by optical image analysis and sonar reflection.

The other objects and advantages of the present invention will become readily apparent to those skilled in the art from the following detailed description wherein only the preferred embodiments of the invention are shown and described, simply by way of illustration of the best mode contemplated of carrying out the invention. As will be realized, the invention is capable of other and different embodiments, and that several details are capable of modifications in various obvious respects, all without departing from the invention. Accordingly, the drawing and description are to be regarded as illustrative in nature, and not as restricted.

BRIEF DESCRIPTION OF DRAWINGS

FIGS. 2A-2C are sectional illustrations of a tab hook assembly of the tester of FIG. 1;

BEST MODE FOR CARRYING OUT THE INVENTION

Figure 1:
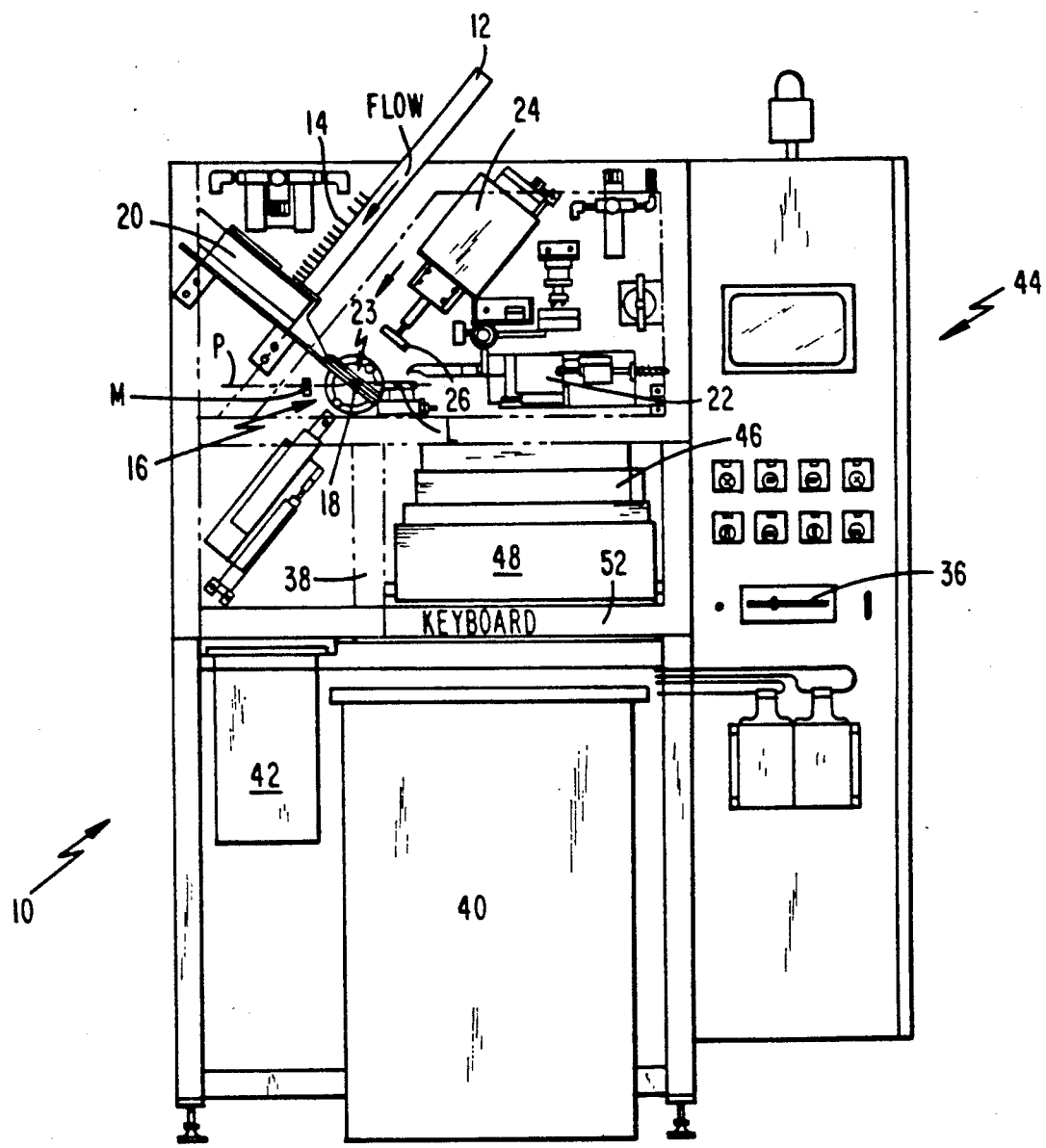
FIG. 1 is a side elevational view, partly schematic, of an automated end tab pull tester incorporating the present invention.
Figure 3A:
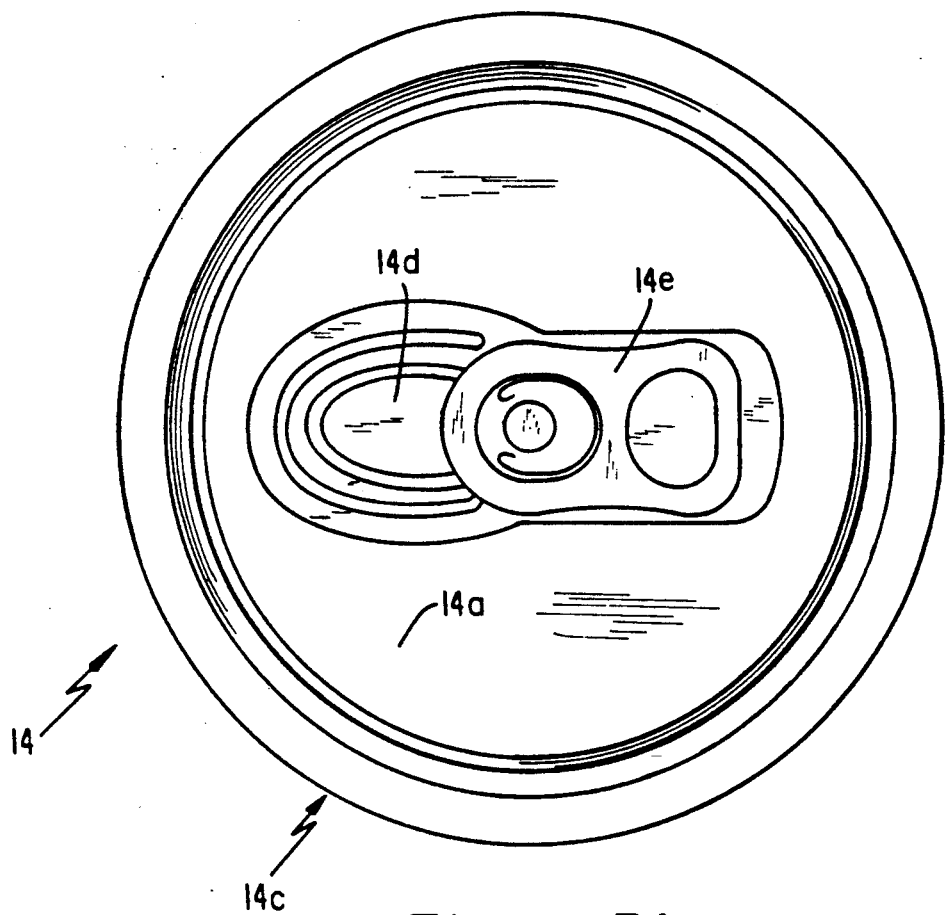
FIGS. 3A and 3B are top and elevational sectional views of a typical can end to be tested with the tester of FIG. 1.
Figure 3B:
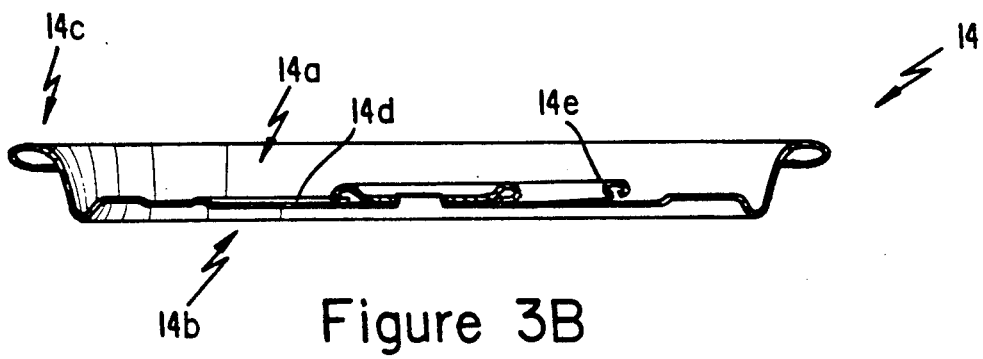

A can end tester into which the present invention may be incorporated is depicted in FIG. 1 as an apparatus 10 for measuring the force applied to a pull tab to form an opening in a can end. A feed chute 12 holds a supply of can ends 14 for gravity feed. As best depicted in FIGS. 3A,3B, each can end 14 has an upper surface 14a, a lower surface 14b, a peripheral rim portion 14c, a separable stay-on tab portion 14d and a pull tab 14e secured to the can end and extending over a part of the upper surface. The pull tab 14e may be grasped so as to apply a force acting against the stay-on tab portion 14d to form an opening in the container through the can end.

Holding means 16 is provided for holding a can end 14 at different locations while various tests are performed thereon. The holding means 16 is described more fully in U.S. Pat. 4,850,230, issued July 25, 1989, the disclosure of which is hereby incorporated by reference herein in its entirety. Basically, the holding means 16 is rotatable about horizontal axis 18 from a position depicted in FIGS. 1 and 5 where it receives a can end to be tested from a part feeder means 20, to a vertically upright position as depicted in FIGS. 2A-2C where the pull tab 14e of the can end will be engaged by a hook assembly 22 described more fully below. The part feeder 20, which may be conventional, separates one of the can ends 14 from the feeder magazine or chute 12 and feeds the end through an outlet chute 20' into the holding means 16. The holding means 16 is formed with an opening 23 which enables a substantial portion of the center of the can end 14 including the pull tab 14e to be exposed along a horizontal path defined by reference letter P which extends continuously and uninterruptedly between light source/sensor L and mirror M of the invention.

An orienter assembly 24 has a pull tab positioning head 26 dimensioned so that it may pass through the opening 23 and move into contacting relationship with the upper surface 14a and pull tab 14e of the can end 14. The pull tab positioning head 26 is rotated when in contact with the upper surface and pull tab 14e to position the tab of each can end at the same predetermined position.

Force measuring means 30 is provided for measuring the forces generated during the formation of the opening in the can end 14. The force measuring means 30 has a pivotally mounted hook member 32 depicted in FIGS. 2A-2C which is positioned between the upper surface 14a and the pull tab 14e to restrain movement of the pull tab (i.e. FIG. 2B) during the force measuring operation. After the hook member 32 has been moved into this position, the holding means 20 is rotated to move the upper surface 14a in the direction A away from the pull tab 14e, generating the forces to be applied to the stay-on tab portion 14d to force the opening in the can end. The force measuring means 30 has a strain gage load cell 34 measuring the restraining force on hook member 32 as it prevents movement of the pull tab 14e. The force measuring means 30 is operatively associated with recording means which may include data storage means (e.g., a hard drive 36) for continuously recording the forces applied during the opening operation. Discharge means 38 is provided for separating the can ends 14 into passed or failed parts bins 40,42.

The operation of the apparatus is described in detail in the '230 patent and such disclosure is hereby incorporated by reference herein in its entirety. The recording means 36 continuously records all restraining forces during the rotation of the holding means through 90°.

The apparatus is further provided with a host computer system 44 which, in a known manner, controls an electronic reproducing device, such as the hard disk 36, and a recorder-printer 46 which continuously prints the information on paper from a paper box holder 48. The test results (such as forces measured by the load cell 34) and the test parameters (such as degree of rotation of the can end) are transmitted as signals to the hard disk 36 (or a floppy disk) for storage.

Figure 4:
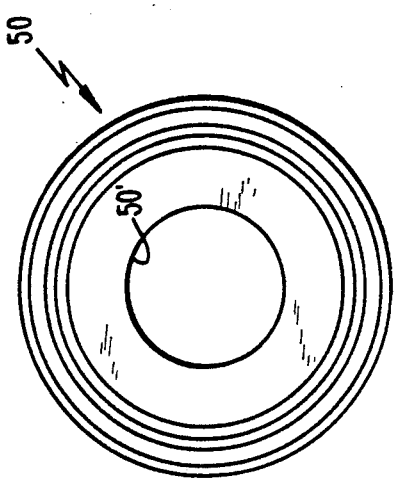
FIG. 4 is a top plan view of a special coded end in accordance with the present invention.

A plant technician or operator having responsibility for monitoring one or more can end forming machines will periodically remove sample ends 14 from the current production of manufactured ends where he/she will take and insert the set of sample ends into the system infeed hopper 12 of the tester. A special coded end 50 as depicted in FIG. 4 will be placed by the technician on top of the sample set 14. The technician will then input to the electronic reproducing device 36, via the host computer 44 and through a keyboard 52, various types of production data information to the system such as the plant technician's identifier (clock number); the machine from which the samples were taken; the type of inspection (e.g., opening or tab strength); and current shift. The technician will then return to his normal duties. Plural sets of samples 14 may be added to the infeed stack 12 by one or more plant technicians. Each set is separated from the adjacent set by one of special coded ends 50. This production data is correlated with the test data by the host computer 44. In the manner described below, the special coded end 50 provides an accurate means for signalling the host computer 44 as to the completion of testing of a particular sample set from a particular machine.

The host computer 44 will monitor all conditions and control events within the testing apparatus 10 as follow:

(1) The system will separate the bottom end from the stack 14, orient it, and transfer to the inspection stage.

(2) The inspection commences and is completed.

(3) The inspected end is then transferred to the discharge stack 38 where it is deposited into either a "passed" or "failed" bin 40,42.

(4) The next end is then processed as listed in items (1)-(3), supra. This process is continuous.

Figure 5:
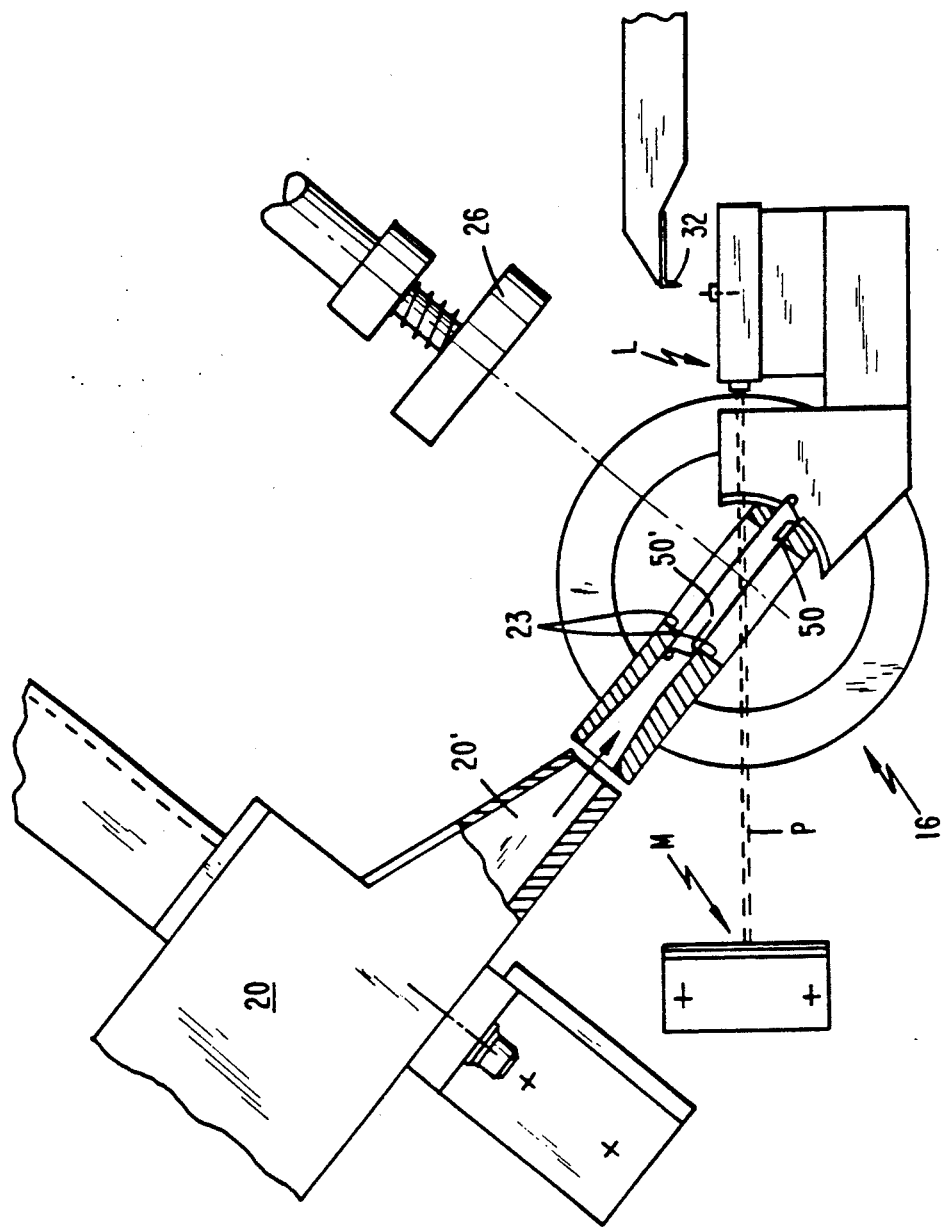
FIG. 5 is a detailed sectional illustration of a can end depicting placement of a light sensor and mirror in relation to a can end holding means.

In accordance with the present invention, a light source L (e.g., a commercially available infra-optical switch) is mounted on one side of the holding means 20 to transmit a beam of light along path P through the opening 23 which beam of light would pass through the hole 50' in a special coded end 50 (when present) to impinge upon a mirror M mounted on the opposite side of the opening 23 as best depicted in FIG. 5. The light source L also includes a light sensor responsive to reflection of light by mirror M through the special coded end hole 50'. The light sensor L will transmit a signal to the host computer 44 upon detection of the special coded end 50 in the aforesaid manner, signifying the end of testing of a sample set and that the next end will be the start of a new sample set.

As mentioned above, the operational sequence of the various components of the testing apparatus may be controlled by the host computer system 44. Such a system could be a PC Bus industrial microcomputer system using a CPU card containing an 80286 cpu chip which runs a DOS operating system. The majority of the software would be located on a hard disk drive but be on an EPROM chip permanent ram memory. The control system could utilize a 1.44 megabyte 3½" floppy disk for user input and for data output.

Apart from the light source/sensor L and mirror M arrangement of the invention, the testing apparatus may otherwise be identical in all respects to the FIG. 1 embodiment of the testing apparatus disclosed in the '230 patent. Thereby, the FIG. 1 embodiment is hereby incorporated by reference herein in its entirety.

It will be readily seen by one of ordinary skill in the art that the present invention fulfills all of the objects set forth above. After reading the foregoing specification, one of ordinary skill will be able to effect various changes, substitutions of equivalents and various other aspects of the invention as broadly disclosed herein. It is therefore intended that the protection granted hereon be limited only by the definition contained in the appended claims and equivalents thereof.

I claim:

1. In a can end testing apparatus performing a predetermined test on a can end manufactured in a can end forming machine to determine whether the can end satisfies a particular production parameter, said apparatus including a feed chute into which a set of sample can ends to be tested is inserted as a stack; a part feeder means for removing a next in-line can end to be tested from the stack; means, receiving the end from the part feeder means, for holding the end while said predetermined test is being performed on it; testing means for applying said predetermined test to said end in the holding means; means for storing data representative of the results of said predetermined test; host computer means for retrieving data from said data storing means and for coordinating said test data with production data indicative of at least the machine manufacturing said end; and means for discharging said can end from the testing apparatus; the improvement comprising sensing means, located downstream from the feed chute, for sensing the presence of a physical characteristic of a material object positioned in the stack which physical characteristic signifies the completion of testing of a particular sample set, and means for signaling the host computer means of said completion to thereby enable precise correlation of said test data with the production data.

2. In the can end testing apparatus of claim 1, wherein said material object is a coded can end having a preformed hole and said sensing means includes a photoelectric sensor and means for emitting a beam of light onto each can end, including the coded can end, which beam shines through the hole to be impinged on the sensor when the coded end is present.

3. In the apparatus of claim 2, wherein said coded can end is colored differently from the can ends within the set to enable visual identification of the coded can end.

4. In the apparatus of claim 2, wherein said holding means includes a bail assembly into which the can end or material object enters for interrogation by the sensing means.

5. In the apparatus of claim 1, wherein said coded can end is colored differently from the can ends within the set to enable visual identification of the coded can end.

6. In the apparatus of claim 1, wherein said holding means includes a bail assembly into which the can end or material object enters for interrogation by the sensing means.

7. Apparatus for measuring the force applied to a pull tab to form an opening in a container lid comprising a feed chute for holding a supply of container lids, each of which has an upper surface, a lower surface, a peripheral rim portion, a severable tab portion and a pull tab secured to said container lid and extending over a part of said upper surface which pull tab is adapted to be grasped so as to apply a force thereto acting against said severable tab portion to form an opening in said container lid; holding means for holding one of said container lids while operations are performed thereon; said holding means having at least one opening formed therein so that a substantial portion of said upper surface and all of said pull tab are exposed; feed means for separating one of said container lids from said supply thereof and feeding said one of said container lids to said holding means; stop means for cooperating with said holding means for positioning said one container lid so that said substantial portion of said upper surface and said pull tab are exposed through said at least one opening; orienting means for contacting said pull tab and said upper surface to position said pull tab at a predetermined location in said holding means; force measuring means having a portion thereof in contact with said pull tab for measuring the forces generated on said pull tab during the formation of said opening in said container lid; force applying means for causing relative movement between said container lid and said pull tab to apply a force to said severable tab portion to form said opening in said container lid; recording means for recording the forces applied to the pull tab during the formation of the opening in said container lid; and discharge means for discharging said opened container lid to a hopper; the improvement comprising sensing means, located downstream from the feed chute, for sensing the presence of a physical characteristic of a material object positioned in the stack which physical characteristic signifies the completion of testing of a particular sample set, and means for signaling a host computer means of said completion to thereby enable precision correlation on said test data with production data.

8. In the apparatus of claim 7, wherein said material object is a coded can end having a preformed hole and said sensing means includes a photoelectric sensor and means for emitting a beam of light onto each can end, including the coded can end, which beam shines through the hole to be impinged on the sensor when the coded end is present.

9. In the apparatus of claim 8, wherein said coded can end is colored differently from the can ends within the set to enable visual identification of the coded can end.

10. In the apparatus of claim 7, wherein said coded can end is colored differently from the can ends within the set to enable visual identification of the coded can end.

11. A method of identifying whether the termination of testing a sample set of can ends, manufactured by a particular can forming machine, has occurred within a can end testing apparatus, comprising the steps of:
a) having a plant technician or operator insert said sample set of ends into a system in the feed hopper of the can end testing apparatus;
b) having said plant technician insert a special coded can end on top of the sample set;
c) having said plant technician input production data indicative of at least one of the plant technician's identity, the particular forming machine the can end comes from, and production shift;
d) sequentially feeding the ends within the set into the testing apparatus and performing a predetermined test on the can end;
e) determining completion of testing of said sample set by sensing the feeding of said special coded can end into said testing apparatus.

12. The method of claim 11, wherein batches of sets separated by coded ends are inserted into the infeed hopper.

13. The method of claim 12, wherein said batches are inserted into the hopper by different plant technicians monitoring different forming machines.

14. The method of claim 12, comprising the further step of coordinating the test data with the production data inputted by the plant technician in step (c), repeating steps (d) and (e) with the next in-line set of ends.

15. The method of claim 14, wherein sensing occurs by sensing the presence of a physical characteristic of the special coded can end which physical characteristic signifies the completion of testing of the said particular sample set.

16. The method of claim 15, wherein the physical characteristic is a hole formed in the special coded end and sensing occurs by transmitting a light beam in the direction of the end beam supplied to the testing apparatus and determining whether the light beam passes through said end.

17. The method of claim 15, wherein said special coded end is colored differently from the remainder of the can ends within the sample set.

* * * * *